(12) United States Patent  
Boll et al.

(10) Patent No.: US 7,112,195 B2  
(45) Date of Patent: Sep. 26, 2006

(54) ESOPHAGEAL LESION TREATMENT METHOD

(75) Inventors: James Boll, Newton, MA (US); Evan Sherr, Ashland, MA (US); Jamie Koufman, Winston-Salem, NC (US); George Cho, Hopkinton, MA (US)

(73) Assignee: Cynosure, Inc., Westford, MA (US)

( * ) Notice: Subject to any disclaimer, the term of this patent is extended or adjusted under 35 U.S.C. 154(b) by 29 days.

(21) Appl. No.: 10/728,258

(22) Filed: Dec. 4, 2003

(65) Prior Publication Data

US 2004/0210278 A1 Oct. 21, 2004

Related U.S. Application Data

(60) Provisional application No. 60/464,181, filed on Apr. 21, 2003.

(51) Int. Cl.  
A61B 18/22 (2006.01)  
A61B 18/00 (2006.01)

(52) U.S. Cl. .............................. 606/15; 128/898; 606/2

(58) Field of Classification Search ................ 128/898; 606/15  
See application file for complete search history.

(56) References Cited

U.S. PATENT DOCUMENTS

| | | | | |
|---|---|---|---|---|
| 4,878,725 A | * | 11/1989 | Hessel et al. | 385/27 |
| 4,887,600 A | * | 12/1989 | Watson et al. | 606/2.5 |
| 5,125,925 A | * | 6/1992 | Lundahl | 606/15 |
| 5,409,483 A | * | 4/1995 | Campbell et al. | 606/15 |
| 5,584,803 A | * | 12/1996 | Stevens et al. | 604/6.16 |
| 5,623,940 A | * | 4/1997 | Daikuzono | 600/439 |
| 6,013,053 A | * | 1/2000 | Bower et al. | 604/96.01 |
| 6,027,499 A | * | 2/2000 | Johnston et al. | 606/22 |
| 6,352,503 B1 | * | 3/2002 | Matsui et al. | 600/104 |
| 6,423,055 B1 | * | 7/2002 | Farr et al. | 606/15 |
| 6,454,790 B1 | * | 9/2002 | Neuberger et al. | 607/88 |
| 6,635,052 B1 | * | 10/2003 | Loeb | 606/15 |
| 6,635,068 B1 | * | 10/2003 | Dubrul et al. | 606/200 |
| 6,743,197 B1 | * | 6/2004 | Edwards | 604/103.01 |
| 6,755,849 B1 | * | 6/2004 | Gowda et al. | 607/89 |
| 6,792,979 B1 | * | 9/2004 | Konya et al. | 140/92.1 |
| 2002/0143323 A1 | * | 10/2002 | Johnston et al. | 606/21 |
| 2003/0060813 A1 | * | 3/2003 | Loeb et al. | 606/17 |
| 2003/0191363 A1 | * | 10/2003 | Boll et al. | 600/101 |
| 2003/0199913 A1 | * | 10/2003 | Dubrul et al. | 606/191 |
| 2004/0073088 A1 | | 4/2004 | Friedman et al. | 600/114 |
| 2004/0082859 A1 | | 4/2004 | Schaer | 600/459 |
| 2004/0087936 A1 | | 5/2004 | Stern et al. | 606/41 |
| 2004/0249243 A1 | * | 12/2004 | Kleiner | 600/115 |

FOREIGN PATENT DOCUMENTS

GB 2390545 A * 1/2004

* cited by examiner

Primary Examiner—Henry M. Johnson, III  
(74) Attorney, Agent, or Firm—Don Halgren

(57) ABSTRACT

Apparatus for the treatment of Barrett's esophagus, including: an inflatable balloon for insertion into the esophagus, an endoscope for passing inside the balloon on a distal end thereof, a laser fiber apparatus for insertion within the balloon in the esophagus, and a balloon inflation/deflation means in fluid communication with the balloon for inflating and emptying the balloon into and out of contact with the walls of the esophagus to be treated. The balloon may occlude the stomach from the esophagus during treatment.

11 Claims, 7 Drawing Sheets

ESOPHAGEAL LESION TREATMENT METHOD

BACKGROUND OF THE INVENTION

1. Field of the Invention

This invention relates to the treatment of Esophageal Dysplasia, otherwise known as Barrett's Esophagus, based upon provisional application serial No. 60/464,181, filed 21 Apr. 2003, and incorporated by reference in its entirety.

2. Prior Art

Barrett's Esophagus is a pre-malignant condition of the mucosa associated with gastroesophageal reflux disease (GERD). The term GERD refers to the reflux of gastric acid fluids from the stomach into the swallowing tube or esophagus and is typically called "heartburn". Barrett's Esophagus is typically diagnosed by an endoscopic examination and biopsy wherein a tube equipped with imaging optics on its distal tip is inserted in a patient's mouth and into the esophagus to view and biopsy the lining of the esophagus. An abnormal lining is seen as pink or reddish (often described as salmon colored), which would replace a normal whiteish color of the lining of the esophagus. Such an abnormal lining may cover a short distance, less than three inches, or a longer distance of the esophagus from the gastroesophageal junction, that is, where the esophagus meets the stomach. A biopsy of the pinkish lining may indicate the presence of intestinal type cells which are otherwise called goblet cells. The presence of such goblet cells indicates the likelihood of Barrett's Esophagus. Barrett's tissue may also contain disorganized abnormal blood vessels which results in the lesion's characteristic color.

Dysplasia in Barrett's Esophagus is a change in the cells that line the esophagus, wherein those cells actually appear abnormal. These cellular changes, or dysplasia may indicate a pre-cancerous condition. Surgical treatment of GERD may be called anti-reflux surgery. Such an operation is called fundoplication which is done to stop the reflux of acid. Such an operation involves wrapping of the upper stomach (the fundus) around the lower end of the esophagus. This wrap tightens the lower esophageal sphincter to minimize or prevent the reflux of stomach contents into the esophagus. While this may limit acid exposure of the esophagus, it does not effect the treatment of Barrett's esophagus. The latest treatment modality for Barrett's esophagus includes surgical excision and ablative therapy via photodynamic therapy. Diagnosis as early as possible is important to detect and minimize any cancer related problems which may occur.

It is an object of the present invention to improve the methodology of treating Barrett's Esophagus; and it is a further object of the present invention to provide a treatment for Barrett's Esophagus not shown or suggested in the prior art.

BRIEF SUMMARY OF THE INVENTION

The present invention relates to laser apparatus for providing endoscopic laser treatments for dealing with abnormal mucosal tissue, particularly esophageal dysplasia, otherwise known as Barrett's Esophagus, utilizing a delivery apparatus, for example, a laser delivery apparatus, to permit clear visualization of the esophagus, eliminating or reducing reflux during that visualization process, delivering a laser or other treatment of the esophagus, and reducing the movement of the esophageal wall to permit accurate laser dosimetry.

A clear balloon in the present invention is inflated when near the lesion in the esophagus to permit the visualization therethrough. Laser energy is transmitted through that balloon subsequent to the visualization and targeting of a lesion thereby. A balloon which is positioned in the lower esophagus is inflated to distend and partially or completely seal the esophagus from the stomach. Any reflux is kept out of the visualization field by the balloon. The lesion may be seen through the balloon and outside thereof by an endoscope arranged within that balloon. The laser treatment beam from the laser apparatus may be positioned within that balloon upon detection of the lesion target.

A flexible endoscope with a working channel would be utilized to introduce a balloon and a laser delivery optical fiber to be inserted within the patient's esophagus. The endoscope would be pressed against the distal end of the balloon. The scope would be utilized to permit visualization and guidance of the balloon. Once within the desired location of the esophagus, the balloon would be inflated with a cooled fluid such as saline, water or a gas or the like, and the scope would be retracted to a position within the inflated balloon. The visualization scope and a laser fiber may be steered to the appropriate spot, and lasing would be permitted through the balloon wall. Air and or other fluid may be purged from the balloon by pumping in a saline fluid through the fiber-working channel and removing the air through an annulus around the scope sheath.

Because laser energy has an inherent selectivity to heat the target tissue (vasculature) and not the surrounding tissue, it is not necessary to precisely target the lesion separate from its normal borders. In one preferred embodiment the laser light may be directed towards the general area of treatment, bathing both normal and abnormal tissues, with the precision targeting in this embodiment left to the selective nature of the laser apparatus. In this embodiment, it is possible to do a procedure without direct visualization: i.e. Introducing the laser delivery fiber and expose the entire lumen. This method may be referred to as the "blind" procedure. A balloon would still be utilized for opening up and blocking the esophagus to enhance the coupling of laser energy to the esophageal wall with more controlled dosimetry.

A balloon of this type would have an inflated diameter of between 10 to 40 mm. Alternatively, the balloon could be elastic and a change in pressure of the saline or of the air in the balloon will proportionately change the diameter of the balloon. The balloon in its deflated state and its associated sheath must be less than about six mm in diameter to facilitate passage through the nasal cavity. The balloon would have a preferred length of between 5 to 50 mm. The balloon in a further embodiment may have a window tip to ensure proper visualization of the entry process during insertion of the balloon into the esophagus. The tip of the balloon may serve an anchor within the esophageal sphincter. In another embodiment, no separate tip is required and the balloon is simply stretched over the imaging optics and laser through the balloon after the balloon has been inflated. Such an arrangement would permit lasing in the distal direction through the distal portion of the balloon in addition to lasing through the transparent walls of the balloon. Utilizing a bare tip optical fiber, the entire circumference of the sphincter, shaped as a forward hemisphere may be exposed to the laser for treatment thereof, as well as its sidewalls through a steering scope and laser delivery fiber at an angle which deviates from the longitudinal axis of its sheath. Optical fibers for laser delivery may also be utilized in a side firing configuration, to permit better access to the lesions along the esophageal wall not in the axis of the visualization of the endoscope. The sheath may have further lumens or channels therein to be utilized for irrigation and/or aspiration of the space around the scope and the balloon, if necessary.

The use of such a balloon in the esophageal channel permits the purging displacement of esophageal contents "out of the way" so as to smooth the walls thereof by the balloon expansion, for improved visualization and lasing treatment of those esophageal walls. The balloon in a further embodiment, may be filled with a clear fluid (gas or liquid) to permit scattering of the treatment laser light in that balloon for the application of that treatment light onto lesions known as Barrett's Esophagus. After visualization determines the presence of Barrett's tissue, the clear fluid may be purged and replaced with a light scattering (dispersing) fluid for example, a non-toxic lipid. The selective nature of the laser may then be exploited as previously described in the "blind" procedure where all the tissue is bathed in light and the selective absorption and pulse duration guide the precision of 'where and how' the laser energy is absorbed.

Another preferred embodiment of the present invention may include the use of a radiopaque component as part of the balloon to position the balloon when fluoroscopy and not direct optical visualization is being utilized. Once the arrangement is properly positioned, the "blind" procedure may be utilized.

The particular pathologic tissue is affected primarily by a particular laser light energy source. The vascular component of the tissue is to be targeted and ideally, the energy from that source should be specifically absorbed by the vasculature or its components. In one such preferred embodiment, such laser light energy may preferably comprise a laser vascular-specific wave length of for example about 520–650 nm, preferably 585 nm, with a pulse width of for example, between 0.2 and 100 ms, and a laser energy of for example, about 0.5 to 8.0 joules and repetition rates of about 1–10 Hz. A 100–1000 um, preferably 600 um diameter optical fiber is utilized since it is flexible enough to go down an endoscope and big enough to couple a multimode laser.

Treatment energies of between about 0.5 and 1.0 Joules per pulse are typical because the area of exposure is small and the divergence is also small. A fluence of around 0–60 J per square centimeter is considered to be ideal. Lasing ahead and to the side of a balloon an angle of about 45 degrees is one preferred method, because it permits visualization in a proper manner. The outside diameter of the tip of the optical fiber must be smaller than the working channel of the scope, which is between 1 and 5 mm. The divergence of the beam of laser light should be optimized to match the surgical environment, ease of use and desired spot size. The choice of fluid in the balloon will permit control of divergence due to refractive index differences between the fiber and the fluid. For example, water may be utilized to decrease the divergence of the beam due to index matching.

In a preferred embodiment, a 600 um core fiber that launches laser light in air at a deflection angle of about 70 degrees to the fiber axis and with divergence of approximately of about 12 degrees at a half angle. Such divergence may be asymmetric. The deflection angle may be any value between 0 and 180 degrees which optimizes one or both of the surgical goals of treatment and visualization. This would permit optimized visualization for a given combination of fiber and endoscope while getting the treatment spot optimized as well. A further embodiment is one which optimizes the divergence of the laser light to work with any index media inside the balloon in order to obtain the goals of the treatment.

The invention thus comprises a method of treating an esophageal lesion by inserting an inflatable balloon within the esophagus, the esophagus having a wall portion: inflating the balloon; and energizing a laser within the balloon to initiate a treatment of a lesion on the wall of the esophagus. The method may also include one or more of the steps and not necessarily in sequential order: inflating the balloon with a fluid such as for example a gas or a liquid; removing fluid from the balloon; treating the lesion by a light transmitted through a wall of said balloon with or without direct visualization; exposing the lesion with laser radiation through a wall of the inflated balloon; filling the balloon with a laser light-dispersal fluid; visualizing the lesion through the balloon; articulating the fiber to direct the laser beam on a wall of the balloon and the wall of the esophagus; placing the endoscope into the balloon prior to introduction into the patient. Another embodiment may include one or more of the following steps including: placing the balloon on a distal end of an endoscope; inserting the endoscope into an esophagus to be treated; inflating the balloon with a pressurized fluid against the wall of the esophagus; placing a plurality of laser fibers or lumens through the endoscope for treatment of the lesions in the esophagus; purging the esophagus by inflating the balloon against the wall of the esophagus to permit treatment thereof; steering the laser towards a lesion of the esophagus; the fluid may be a liquid or a gas; the liquid may be saline; the balloon preferably has an optically transparent wall; an optically transparent wall of the balloon is preferably in a distalmost position thereon; the balloon may have a distalmost end having a transparent window thereon.

The invention may also comprise an apparatus for the treatment of Barrett's esophagus, including: an endoscope for insertion within an inflatable balloon for insertion into the esophagus; a laser fiber apparatus for insertion within the balloon in the esophagus; and a balloon inflation/deflation means in fluid communication with the balloon for inflating and deflating the balloon. The laser fiber apparatus may be a side emitting laser fiber. A sheath may be arranged for supporting the endoscope. The laser fiber apparatus may be movable. A laser light source is included for generating laser energy comprising a laser light of wave length of about 585 nm and a pulse width of about 0.4 ms. And a laser energy of for example, about 0.5 to about 8.0 joules with repetition rates of about 1–10 Hz.

The invention may also comprise an apparatus for the treatment of Barrett's esophagus, including: an inflatable balloon for insertion into the esophagus; an endoscope for receipt of the balloon; a laser fiber apparatus for insertion within the balloon in the esophagus; and a balloon inflation/deflation means in fluid communication with the balloon for inflating and emptying the balloon. The laser fiber apparatus may be a side emitting laser fiber. A sheath is arranged for supporting the endoscope. The laser fiber apparatus is movable. A laser light source generates a laser wave length of preferably about 585 nm, and a pulse width of about 0.4 ms, and a laser energy of for example, about 0.5 to 8.0 joules and repetition rates of about 1–10 Hz.

The invention may also comprise an apparatus for occluding the esophagus distal to the treatment area. In one preferred embodiment, a balloon would be inserted into the patient and inflated so as to prevent the stomach from communication with the treatment area. Once inflated, the esophagus walls may be treated with a laser apparatus either through direct visualization or through the "blind" technique. The occluding arrangement may be a balloon filled with a fluid such as air or saline, or the occluding arrangement may be a mechanical umbrella-like mechanism which is permitted to expand once it is in the treatment area. After the esophagus has been treated, such a mechanical device would be collapsed and withdrawn from the patient. A yet further embodiment comprises an occluding device which is bioabsorbable, such that after it has been placed in the esophagus and activiated to block the esophagus, the device may be pushed into the stomach after a procedure has been completed.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1A:
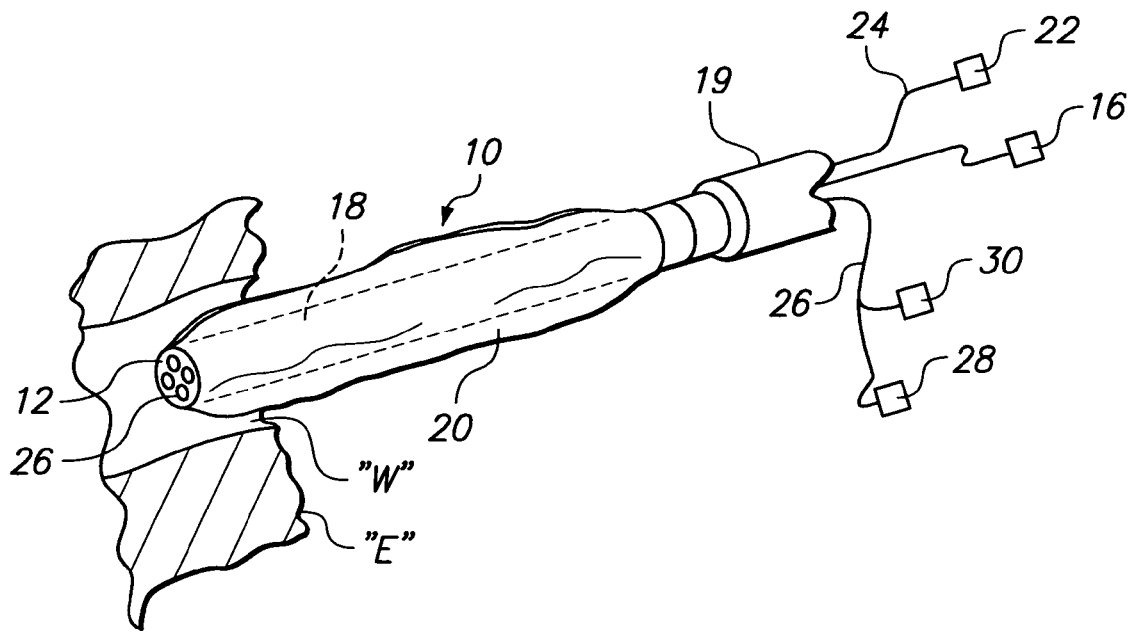
FIG. 1A shows a perspective view of a balloon on the distalmost end of a sheath with a scope arranged therewithin.
Figure 1B:
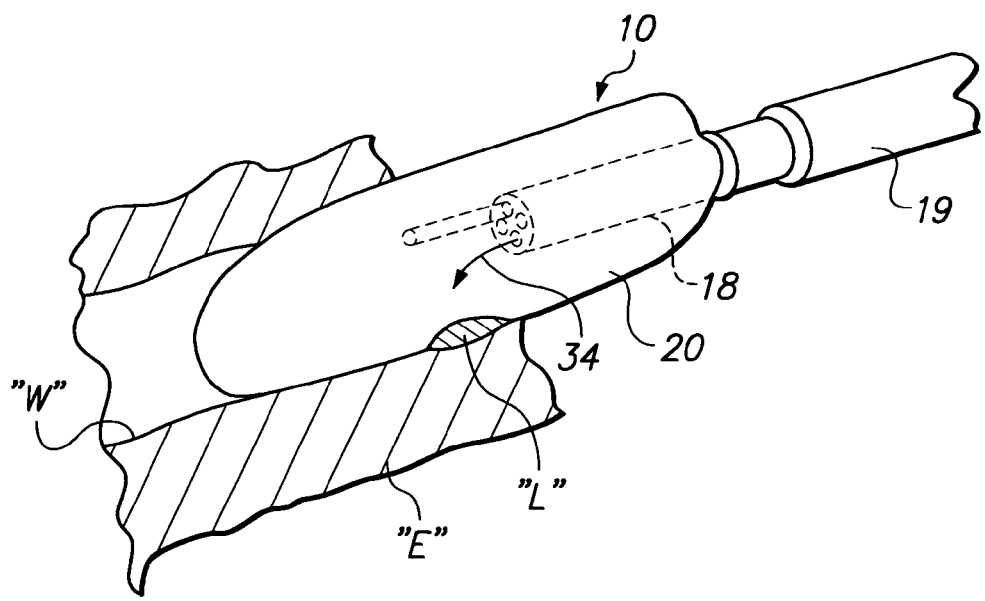
FIG. 1B shows the balloon of FIG. 1 inflated.

Referring now to the drawings in detail, and particularly to FIG. 1A, there is shown an esophageal treating laser apparatus 10 for providing endoscopic laser treatments for dealing with esophageal dysplasia, otherwise known as Barrett's Esophagus. This system utilizes the laser delivery apparatus 10 to permit clear visualization of the esophagus "E", represented in FIGS. 1A and 1B, eliminating or reducing reflux during that visualization process, delivering a laser or effective treatment of that esophagus, and reducing the movement of the wall "W" of the esophagus "E" to permit accurate laser dosimetry. The laser apparatus 10 includes a reciprocably and rotatably movable optical emitter 12 comprised of a flexible fiber optic cable 14 in light communication with a laser light source 16. The laser delivery fiber optic cable 14 may be comprised of an optical fiber or fibers that transmit the laser energy generated by the light source 16 and deliver to the clinical site. The emitter 12 extends through a flexible endoscope 18 which is inserted into a patient's esophagus "E", as represented in FIGS. 1A and 1B, through a sheath 19. The endoscope may contain a coherent optical fiber bundle, preferably for visualization and not for delivery of the laser light. A clear or at least laser light-transparent, inflatable/deflatable balloon 20, which may be elastic, encloses the distalmost end of the sheath 19 and the fiber optic cable 14, as is also represented in FIGS. 1A and 1B. Laser light transparent refers to allowing the laser energy to pass through the wall of the balloon 20 with a minimum of attenuation thus preserving the integrity of the balloon 20. "Clear" in this case may be defined as allowing adequate visualization through the balloon 20 to permit differentiation between normal and abnormal tissue. The balloon 20 is in fluid communication with a temperature and pressure controlled fluid source 22 via a flexible conduit 24 extending through the endoscope 18. The fluid provided to the balloon 20 by the controlled fluid source 22 may be either a light transmissive liquid or a gas, or a combination thereof.

The procedure for one preferred embodiment of the esophageal treating laser apparatus 10 comprises the balloon 20 being pressurized and inflated at least partially, when the distal end of the treatment apparatus 10 is near a treatment site or lesion "L" in the esophagus "E", as represented in FIG. 1B, to permit an optical analysis by the distal end of a movable flexible coherent optical fiber 26 extending through the movable and flexible endoscope 18 to permit visualization of the wall "W" and any lesion "L" through the wall of the inflated balloon 20. The visualization fiber 26 has a proximal end attached to an eyepiece 28 and/or a computer video analyzer 30 to permit physical determination of the physical condition of the wall "W" of the esophagus "E". After a need determination is made of the condition of the wall "W", the light source 16 creates a laser energy output to be transmitted via the optic cable 14 and out the emitter 12, through the wall of the balloon 20 subsequent to the visualization and targeting of a lesion "L" thereby. The balloon 20 in position in the lower esophagus, is inflated, as represented in FIG. 1B, to distend and partially or completely seal the esophagus "E" from the adjacent stomach. Any reflux is thus kept out of the visualization field by the balloon 20, and any residual material is also pressed away by the balloon 20 being inflated against the wall "W" of the esophagus "E". The lesion "L" may be visualized through the balloon 20 and outside thereof by the visualization fiber 26 in the endoscope 18 arranged within the balloon 22. A laser treatment beam 34 may then be directed through the balloon 20 upon detection of the lesion target "L", as represented in FIG. 1B.

Figure 2A:
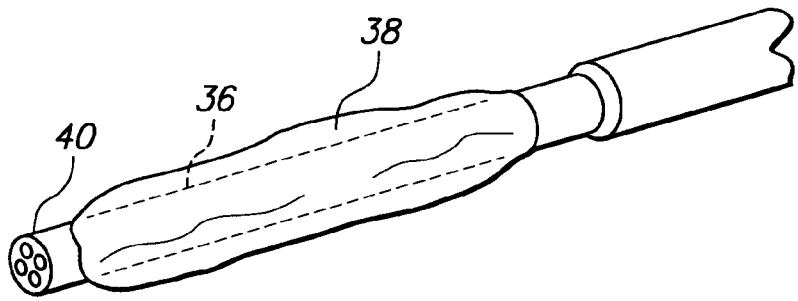
FIG. 2A shows a balloon on a sheath with a distal tip having a scope arranged thereat.
Figure 2B:
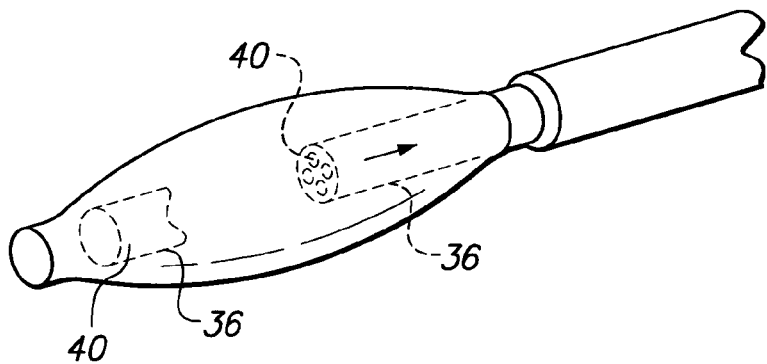
FIG. 2B is a view of the balloon with a scope at its innermost portion while the balloon is inflated.
Figure 3:
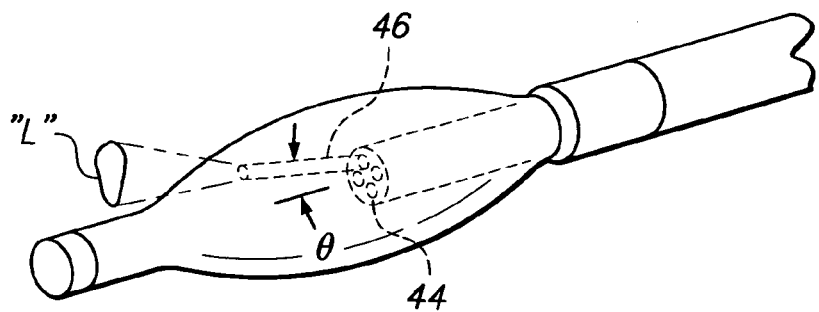
FIG. 3 is the inflated balloon with its distal extended tip and its fiber-optic cable lasing light through a side portion of the balloon.

In a further embodiment as shown in FIGS. 2A and 2B, a flexible, directable endoscope 36 may be utilized through its working channel to permit a balloon 38 and a tip of an endoscope 40 to be inserted within the patient's esophagus, wherein the endoscope 40 would be pressable directly against the distal end of the balloon 38, as represented in phantom lines in FIGS. 2A and 2B, and also in as endoscope 18, as represented in FIG. 1A. The endoscope 18 or 40, would be utilized to permit visualization and guidance of the balloon 20/38, as represented for example, in FIGS. 1A and 2A. The balloon 20 is required to be deflated to pass through the narrow anatomy of the nasal passages. The collapsed balloon 20 or 38, would be furled, folded or stretched over the sheath 19, and should not be larger than about 5×7 mm in cross section with smaller sizes preferred. Once within the desired location of the esophagus, the balloon 20/38 would be inflated with a fluid such as saline, water or a gas or the like, as represented in FIG. 1B, and the endoscope 36 would be retracted in the sheath 19 to a more "proximal" position within the inflated balloon, as represented in the FIG. 2B. The visualization port 44 and a laser fiber 46 may each be individually steered or collectively steered by the endoscope 36 to the appropriate spot, and laser light would be permitted through the wall of the balloon 38, as represented in FIG. 3.

Figure 4:
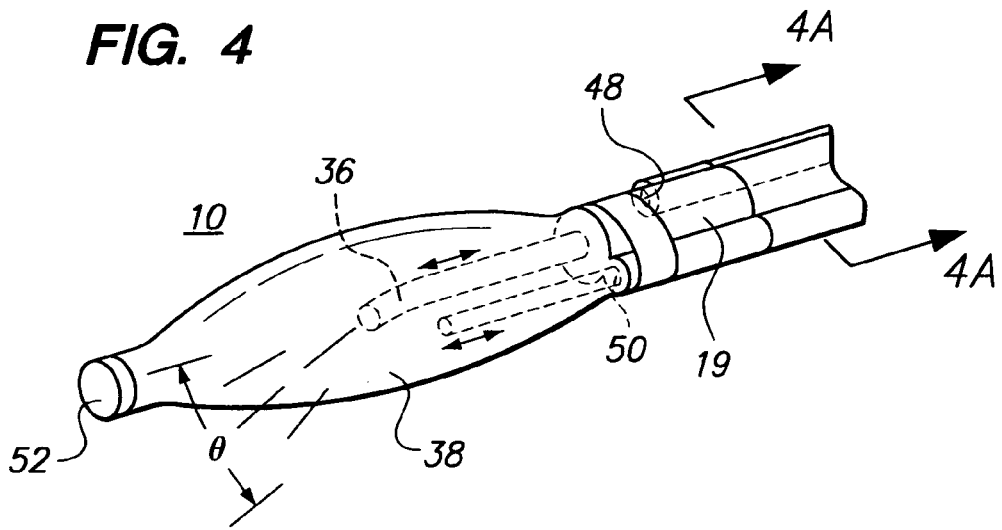
FIG. 4 is a perspective view of an inflated balloon on a sheath having a number of working channels therewith.

A further preferred embodiment of the present invention utilizes air and/or other fluid being purged from the balloon 38 by pumping in a saline fluid through a fiber working channel 48 on the sheath 19, proximal to and outside of the balloon 38 and a further lumen 50 in communication with the interior of the balloon 38, as represented in FIG. 4, to permit removal of the fluid/gas through the endoscope 36 sheath annulus. Such a sheath 19 to effect this preferred embodiment, has a proximal end represented in FIG. 5B, having a scope conduit 58 and an optic lumen conduit 60, with a saline connector 62 arranged with the conduit 58 and the optic lumen 60. The saline or other fluid media permits proper visualization without condensation or fogging of the image. The fluid may also serve as a heat sink to remove unwanted and potentially harmful thermal components induced into the balloon or the tissue by the laser energy. The fluid media may also serve to modify the divergence of a laser beam within the balloon 20.

Figure 5A:
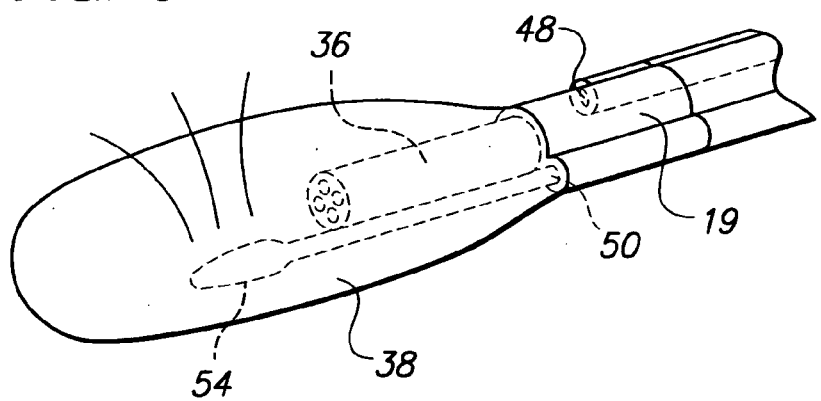
FIG. 5A is a view of an inflated balloon on the distal end of a sheath with a side emitting laser fiber therewith.
Figure 5B:
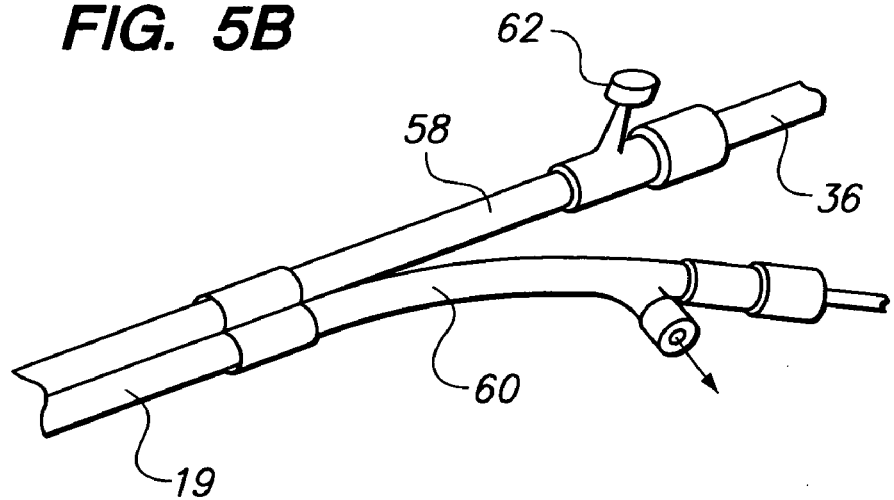
FIG. 5B is a perspective view of a multiple Luer lock arrangement for servicing the inflatable balloon arrangement.
Figure 6:
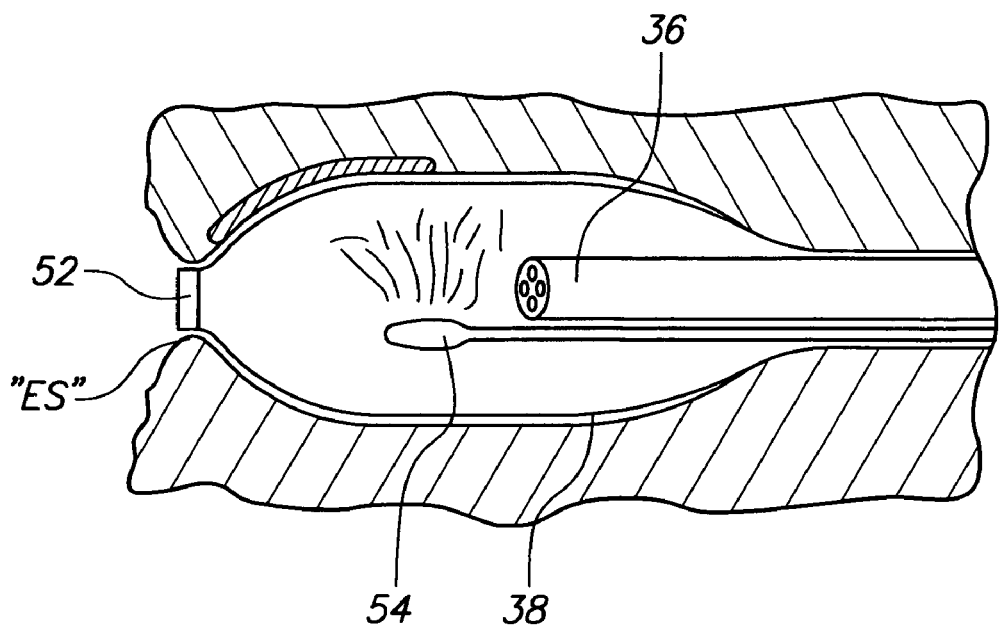
FIG. 6 is a side elevational view of a scope and optical fiber in the sphincter and the lumen of an esophagus.

The balloon 38 in FIG. 4 is shown with an extended distalmost window 52, which may provide clearer light transmission or engagement by the distalmost end of the endoscope 36 for more perfect directionality or steering of the assembly 10. A balloon 38 of this type would have an inflated diameter of between about ten to about 40 mm. The balloon 38 in its deflated state, as represented in FIGS. 1A and 2A and its associated sheath 19 must be about six mm in diameter. The balloon 38 would have a preferred length of between 5 to 50 mm, as represented by "LI" in FIGS. 9 and 10. This balloon 38 may have its distal window 52 to also ensure proper visualization of the entry process during insertion of the assembly 10, including the movement of the balloon 38 into the esophagus. The extended window 52 of the balloon 38 may serve an anchor within the esophageal sphincter "ES", as represented in FIG. 6. Such an arrangement would permit lasing in the distal direction through the distal portion of the balloon 38, or permit sidewise lasing utilizing a side firing laser fiber 54, as represented in FIGS. 5A and 6, in a further embodiment thereof.

Figure 4A:
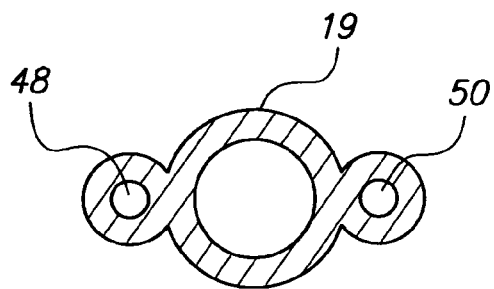
FIG. 4A is a sectional view taken in FIG. 4.
Figure 7:
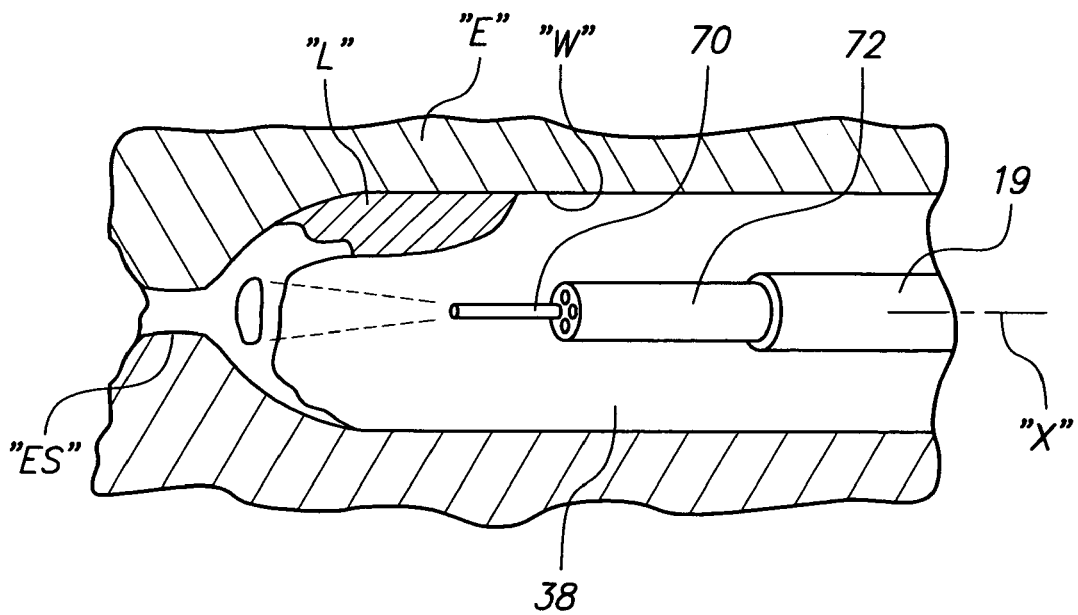
FIG. 7 is a further view of a balloon and fiber firing laser light onto a spot on a vascular lesion.

Utilizing a bare tip optical fiber 70, as represented in FIG. 7, the entire circumference of the esophageal sphincter "ES", shaped as a forward hemisphere may be exposed to the laser for treatment thereof, as well as its sidewalls through a steering endoscope 72 and fiber 70 at an angle which deviates from the longitudinal axis "X" of the endoscope 72 and its sheath 19. An arrangement of optical fibers 54 for lasing may be utilized also in a side firing configuration, as represented in FIGS. 5A, and 6, to permit better access to the lesions "L" in the wall "W" of the esophagus "E". The sheath 19 may have further lumens or channels 48 and 50 therein to be utilized for irrigation and/or aspiration of the space around the endoscope 36, as represented in FIGS. 4, 4A, and 5A.

The use of such a balloon in the esophageal channel permits the purging displacement of esophageal contents "out of the way" so as to smooth the walls thereof by the balloon expansion, for improved visualization and lasing treatment of those esophageal walls. The balloon in a further embodiment, may be filled with a clear fluid (gas or liquid), for example as shown in FIGS. 5A and 7, to permit dispersing of the treatment laser light in that balloon 38 for the application of that treatment light onto lesions we characterize as Barrett's Esophagus. Such a dispersing fluid may for example be a non-toxic lipid.

The particular pathologic tissue is effected primarily by a particular laser light. Laser light specifically tuned to match the target's characteristics are based on the theory of "selective thermolysis". In one such preferred embodiment, a pulsed dye laser has a wavelength that is tuned to a hemoglobin peak in blood, and its pulse duration is matched to the specific size of the blood vessels. In this way, heat is directed to the vessel wall in an optimal manner, keeping the surrounding tissue unaffected by the localized highly specific targeted tissue receiving thermal treatment. In one such preferred embodiment, such laser light may preferably comprise a laser wave length of for example about 585 mm, with a pulse width of for example, about 0.4 ms, and a laser energy of for example, about 0.5 to 8.0 joules and repetition rates of about 1–10 Hz. A 600 um optical fiber is preferred since it is flexible enough to go down on endoscope and big enough to couple a multimode laser, as may be presented in FIG. 1A. Smaller fibers will permit still greater flexibility.

Treatment energies of between about 0.5 and 1.0 Joules per pulse (8.0 Joules is available from the laser) because the area of exposure is small and the divergence is also small. A fluence of around 0–60 J per square centimeter is considered to be ideal. Lasing ahead and to the side of a balloon an angle of about 45 degrees is one preferred method, because it permits visualization in a more proper manner. The outside diameter of the tip of the optical fiber cannot be larger than the working channel of the scope, which is about 2.2 mm. In one preferred embodiment, the divergence of the beam of laser light should be optimized to speed up the procedure of exposing the lesion and exploit the selective nature of the pulsed dye laser.

A further preferred embodiment of the optical fiber core is about 600 um which launches laser light in air at a deflection angle of about 45 degrees with a divergence maximized to be between about 10 to 90 degrees, as represented in FIG. 3. The divergence may be asymmetric. This would permit optimum visualization for a fiber and endoscope combination while getting the treatment spot optimized as well.

Figure 8:
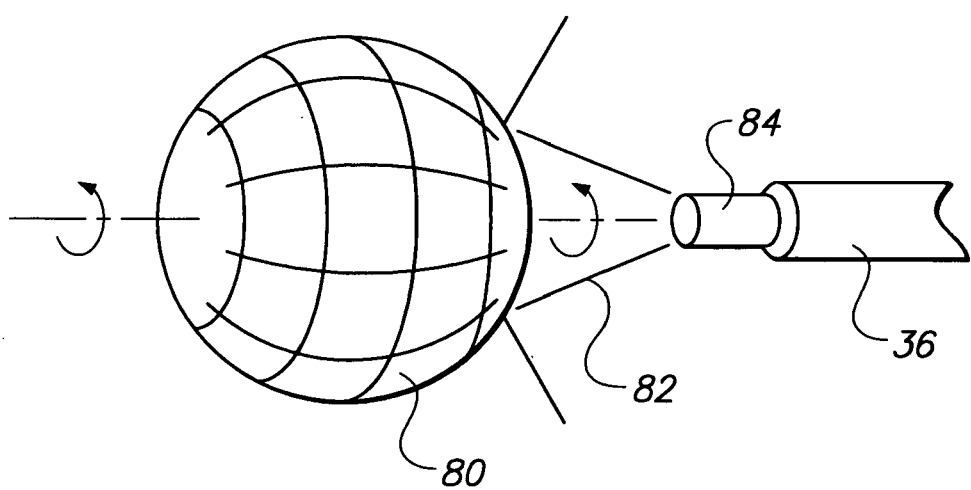
FIG. 8 is a view of a rotating optical arrangement for redirecting laser light.
Figure 9:
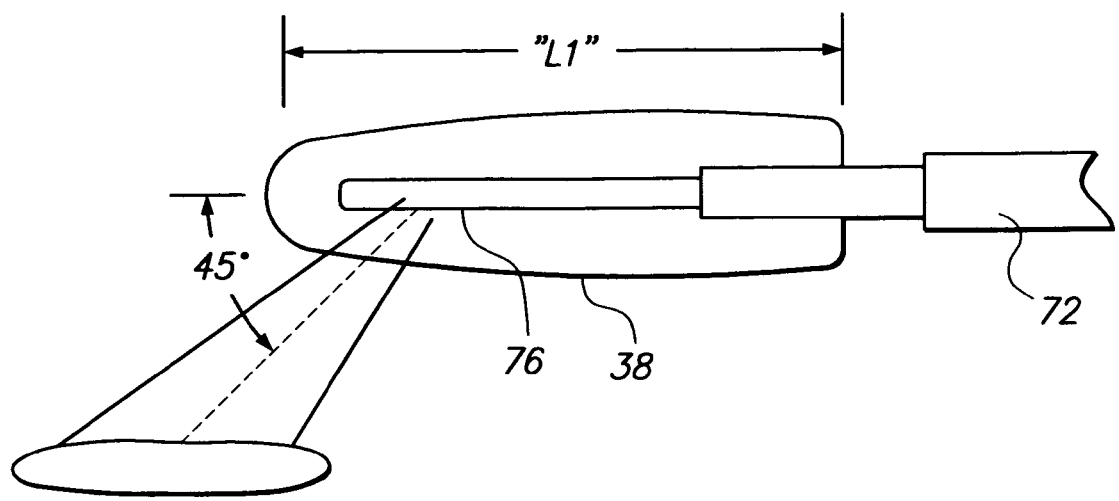
FIG. 9 is a side elevational view of a fiber showing its working distance and directionality of a beam therefrom.
Figure 10:
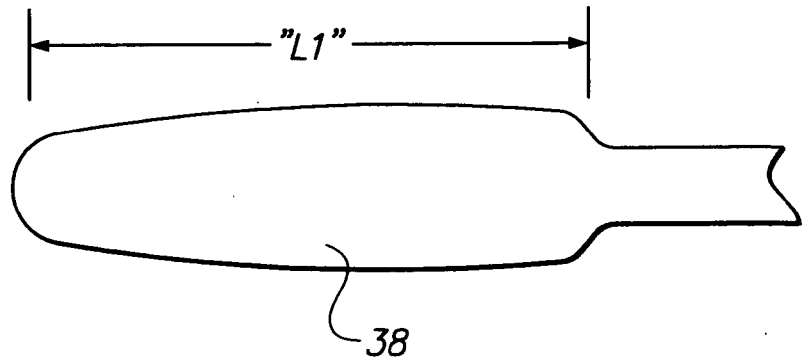
FIG. 10 is a side elevational view of the dimensions of a preferred embodiment of the side firing fiber tip.

A further embodiment of the optical fiber core is one at about 600 um which launches laser light in saline at a deflection angle of about 45 degrees with its divergence maximized to be about 20 degrees, as represented in FIG. 9. A divergence member 80, is shown in FIG. 8, characterized as a rotating reflective member such as for example, a multi-mirror sphere, for deflection of a laser beam 82 from a laser light bearing optic cable 84 would be desired, if such a rotatable deflective member 80 could be arranged at the end of an endoscope 36.

Occlusion of the esophagus may be necessary prior to and during the laser treatment thereof, to permit the esophagus to be cleared and flushed to improve visualization during that treatment period, and to block reflux and/or inflation of the stomach by insufflation.

Figure 11:
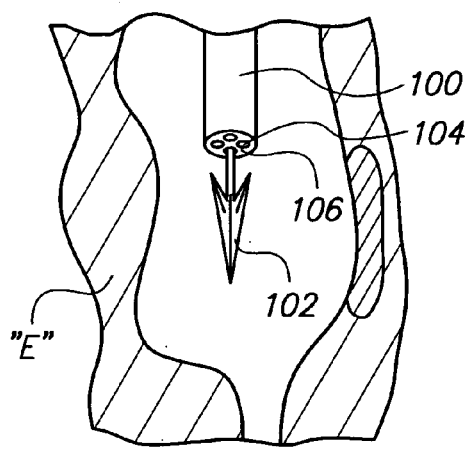
FIG. 11 is an elevational view, partially in section, of a temporary occlusion arrangement for use in treating an esophagus.
Figure 12:
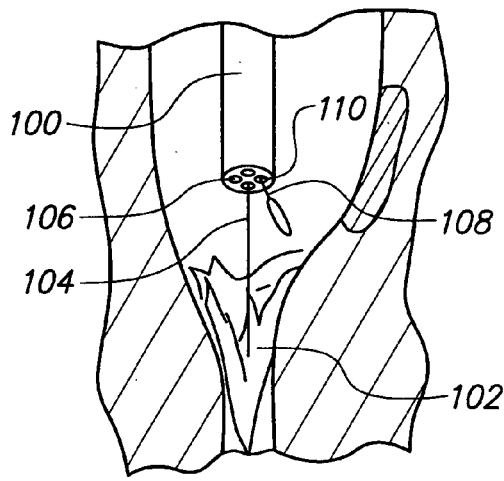
FIG. 12 is a view, similar to FIG. 11, showing the occlusion arrangement in a further step in the esophagus.

FIG. 11 represents a procedure wherein a treatment endoscope 100 is extended into an esophagus "E" to be visualized and treated. An umbrella-like occluder 102 is extended on a multi-shaft control rod 104, from a lumen 106 in the distal end of the endoscope 100. The occluder 102 is caused to "open" and occlude the neck of the esophagus, as represented in FIG. 12. An optical fiber 108 is arranged to extend from a further lumen 110 in the endoscope 100, and lase and thus treat a lesion "L" on the wall "W" of the esophagus "E" as shown in FIG. 12. The umbrella-like occluder 102 may be subsequently collapsed and folded up and retracted back into its lumen 106 for withdrawal from the esophagus.

Figure 13:
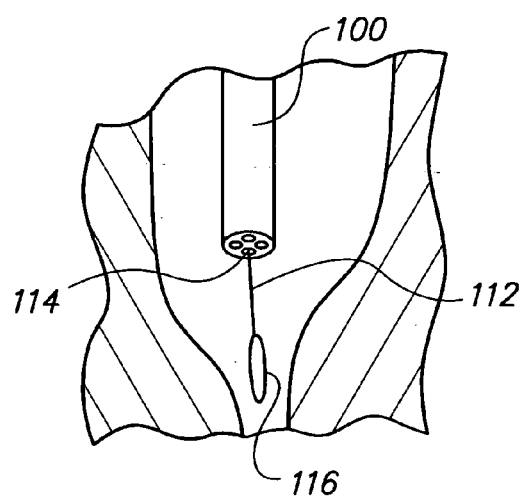
FIG. 13 is an elevational view, partially in section, of a further embodiment of an occlusion arrangement for treating an esophagus.
Figure 14:
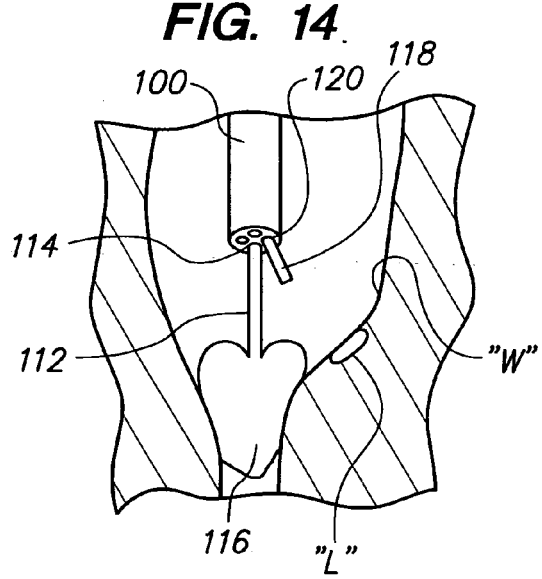
FIG. 14 is a view similar to FIG. 13, showing the further occlusion arrangement in its fully disposed configuration.

A further embodiment of this occlusion treatment is shown in FIG. 13, wherein a microcatheter 112 is shown extending from a lumen 114 in the endoscope 100, which microcatheter 112 has a deflated balloon 116 on its distalmost end. FIG. 14 represents the balloon 116 being inflated through its microcatheter 112, and being disposed in the neck of the esophagus to occlude it, preventing reflux or stomach inflation. An optical fiber 118 is shown extending from a further lumen 120 in the endoscope 100 to lase and treat a lesion "L" on the esophagus wall "W".

Figure 15:
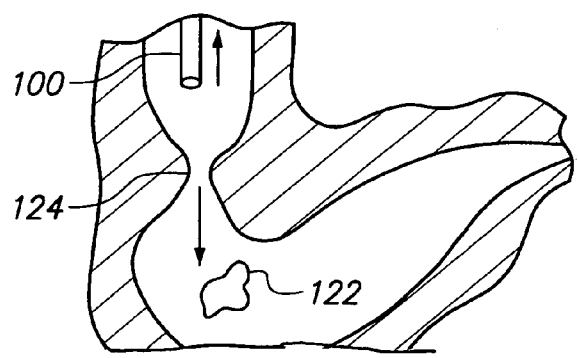
FIG. 15 is an elevation view, partially in section, showing an occlusion arrangement for treating an esophagus in a still further embodiment

FIG. 15 discloses a still further embodiment of an esophageal occlusion arrangement wherein an endoscope 100 has deposited a bioabsorbable or digestable temporary occlusive material 122 to temporarily lodge in the neck of the lower esophagus 124. The endoscope 100 would then lase any lesion by optical means, not shown for clarity, withdrawing from the esophagus, when through, leaving the temporarily occlusive material 122 to dissolve, be digested or pass through the GI tract in due course. Such occlusive arrangements discussed hereinabove may be arranged to extend from a lumen on a side of the endoscope 100, while permitting the balloon of the earlier embodiments to be arranged on the distal end of that scope 100.

Thus what has been shown is a unique array of apparatus and methodologies for visualization and subsequent treatment of an esophagus not shown or suggested in the art.

We claim:

1. A method of treating an esophageal lesion by inserting an inflatable balloon within the esophagus, said esophagus having a wall portion, the method including:
    placing a laser fiber and a visualization port in said balloon;
    inflating said balloon;
    steering said laser fiber and said visualization port individually within said balloon to a lesion, so as to enable treatment of the lesion within the esophagus; and
    transmitting laser energy through said fiber within said balloon to effect laser radiation treatment of a lesion on said wall of the esophagus adjacent said balloon, wherein said laser generates a laser light wavelength of about 520–650 nm and a pulse width of about 0.2–100 ms.

2. The method of claim 1 including:
    inflating said balloon with a fluid.

3. The method of claim 2 including:
    cooling said fluid in said balloon.

4. The method of claim 2 including:
    removing said fluid from said balloon.

5. The method of claim 2 including:
    treating said lesion by a light transmitted through a wall of said balloon.

6. The method of claim 2, including:
    filling said balloon with a laser light-dispersal fluid.

7. The method of claim 1, including:
    emitting said laser radiation through a wall of said inflated balloon.

8. The method of claim 1, including:
    placing at least one laser fiber in said balloon for treatment of said lesions in the esophagus.

9. The method of claim 1, wherein said balloon has an optically transparent wall in a distalmost position of said balloon.

10. The method of claim 1, wherein said laser has an energy of about 0.5 to about 8.0 joules and repetition rates of about 1–10Hz.

11. A method of treating an esophageal lesion by inserting an inflatable balloon within the esophagus, said esophagus having a wall portion, the method including:
    placing an visualization port and a laser fiber in said balloon;
    inflating said balloon;
    bendably steering both said port and said fiber independently of one another in said balloon; and
    transmitting laser energy through said fiber within said balloon to effect laser radiation treatment of a lesion on said wall of the esophagus adjacent said balloon, wherein said laser generates a laser light wavelength of about 520–650 nm, wherein said optical fiber is less than 600 microns in diameter.

* * * * *